(12) United States Patent
Murphy

(10) Patent No.: US 6,219,424 B1
(45) Date of Patent: Apr. 17, 2001

(54) ELECTRONIC STEREOPHONIC AMPLIFIER

(75) Inventor: Edward John Murphy, Rankin Park (AU)

(73) Assignee: Hunter Area Health Service, New Lambton (AU)

(*) Notice: Subject to any disclaimer, the term of this patent is extended or adjusted under 35 U.S.C. 154(b) by 0 days.

(21) Appl. No.: 09/293,359

(22) Filed: Apr. 16, 1999

(30) Foreign Application Priority Data

May 4, 1998 (AU) .................................................... PP6814

(51) Int. Cl.[7] .............................................................. A61B 7/04
(52) U.S. Cl. ............................... 381/67; 181/131; 600/528
(58) Field of Search ............................ 381/67, 1, 28, 381/120; 600/528, 586; 181/131, 137; D24/134; 330/301; 333/4

(56) References Cited

U.S. PATENT DOCUMENTS

| | | | |
|---|---|---|---|
| 3,036,158 | * 5/1962 | Romano | 381/28 |
| 3,222,455 | * 12/1965 | Golik | 381/28 |
| 4,186,273 | * 1/1980 | Dodson | 381/28 |
| 4,438,772 | * 3/1984 | Slavin | 600/528 |
| 4,544,895 | * 10/1985 | Stoker | 330/273 |
| 4,706,777 | * 11/1987 | Baumberg | 181/131 |
| 4,982,435 | * 1/1991 | Kato et al. | 381/28 |
| 4,997,055 | * 3/1991 | Grady | 181/131 |
| 5,386,474 | * 1/1995 | Grodinsky et al. | 381/28 |
| 5,548,651 | * 8/1996 | Long | 381/67 |
| 5,832,093 | * 11/1998 | Bernstein et al. | 381/67 |

FOREIGN PATENT DOCUMENTS

| | | | |
|---|---|---|---|
| PCT/CA96/ 00804 | 12/1996 | (CA) . | |
| 2219944 | * 12/1989 | (GB) | 181/131 |
| 62-104210 | * 5/1987 | (JP) | 381/28 |

OTHER PUBLICATIONS

Shigeru Kazama, M.D., *A New Stereophonic Stethoscope*, Department of Thoracis Surgery, Kitasato University School of Medicine, received for publication Nov. 9, 1989, pp. 837–843.

James H. Philip, ME, MD, and Daniel B. Raemer, PhD, *An Electronic Stethoscope Is Judged Better Than Conventional Stethoscopes For Anesthesia Monitoring*, Bioengineering Laboratory, Department of Anesthesia, Brigham and Women's Hospital, Boston, Mass. accepted for publication Jan. 16, 1986, pp. 151–154.

* cited by examiner

*Primary Examiner*—Xu Mei
(74) *Attorney, Agent, or Firm*—Fulwider Patton Lee & Utecht, LLP

(57) ABSTRACT

A device for use in a stethoscope, the device including two diaphragm-type sound accumulator chambers, one microphone located in each accumulator chamber and one amplification stage connected to each microphone for electronically amplifying audio signals received by the microphones, and an output connector for outputting the amplified audio signals.

12 Claims, 2 Drawing Sheets

ELECTRONIC STEREOPHONIC AMPLIFIER

FIELD OF THE INVENTION

The present invention relates to a device for electrical, stereophonic amplification of sound signals. The present invention is described hereinafter with reference to a stereophonic stethoscope, however, it will be appreciated that the invention does have broader applications.

BACKGROUND OF THE INVENTION

Commonly available stethoscopes provide a monaural sound in that the sound is received in a single sound accumulator such as bell type accumulators or diaphragm type accumulators from which it is "mechanically" provided to ear pieces via ear tubes. A person using such a conventional, monophonic stethoscope will not be able to perceive any directionality of spatiality of the sounds heard. This is because the sound is transmitted to both ear tubes from the one sound accumulator, which acts as the transducer of the sound and therefore becomes a single, intermediate source, in which the sounds generated by the true sources are superimposed.

The perception of directionality and spatiality of the sounds in stethoscopes would allow a differentiation between sounds. E.g cardiac murmurs which are the result of a turbulence of the blood flow in the heart and thus the origins of sounds associated with cardiac murmurs are widely spread whereas the closing and opening clicks of cardiac valves originate from a point source.

To enable perception of directionality and spatiality of sound obtained from a stethoscope, each ear must be provided with sounds transduced by separate sound accumulators and consequently two sound channels must be provided to realise a stereophonic stethoscope.

Stethoscopes providing a stereo signal mechanically have been produced and tested, e.g. reference is made to S. Kazama, "A new Stereophonic Stethoscope", Jpn. Heart J, Vol. 31/6, November 1990.

On the other hand, the use of the conventional, mechanical stethoscope principle has limitations in that sounds can only be heard live in the sense that typically only one person is listening to the sounds and bases his or her diagnosis on his perception of the sounds. To obtain a second opinion of another person, this person must also perform an examination of the patient with the stethoscope therefore the patient is required for a longer time and discomfort may be imposed onto the patient. Therefore, the use of electronic stethoscopes can enable an easy and direct way to record the sounds in one examination which can be replayed to other persons at any time and without further examination of the patient. Further, the electronic audio signal can be more readily made available to more than one person during the examination by transducing the audio signal via speakers. An electronic stethoscope in which a microphone is connected to one precordial stethoscope probe or esophageal probe to monitor a monophonic sound accumulated in the bell or probe electronically via a high quality amplifier is described by J. H. Philip et al in "An electronic stethoscope is judged better than conventional stethoscopes for anaesthesia monitoring", Journal of Clinical Monitoring, Vol. 2/3, July 1986. Previous electronic stethoscopes have employed electronic frequency filtering to selectively amplify sound in the range 37.5–1000 Hz where most heart and lung sounds occur 1, e.g. a bandpass frequency of 0.7–5000 Hz with selectable bass and treble boost/cut circuitry. Other electronic stethoscopes use an upward frequency shift of the entire audio band, aiming to allow improved detection of low frequency sounds. However, the electronic manipulation involved makes for complex and expensive circuitry, as well as increased size, particularly if two units are to be employed for stereophonic stethoscopes. It also requires a significant degree of retraining as the familiar heart and lung sounds may be quite altered.

SUMMARY OF THE INVENTION

In accordance with a first aspect of the present invention there is provided a device for use in a stethoscope, the device including two diaphragm type sound accumulator chambers, one microphone located in each accumulator chamber, one amplification stage connected to each microphone for electronically amplifying audio signals received by the microphones, and an output connector for outputting the amplified audio signals, wherein the amplification sages are connected to one common earth potential and the output connector is arranged in a manner such that the negative inputs of sound transducers which are in use connected to the connector are connected to the common earth potential via an impedance. The positioning of the microphones within the diaphragm type sound accumulator chambers can effect a mechanical filtering means for sounds received by the microphones wherein the filter characteristics can be easily adjusted by varying a pressure on the diaphragms. This can be done by e.g. varying the pressure with which the diaphragm type sound accumulators are pressed against the chest of a patient during examination of a patient.

This can improve a perception of spatiality of the amplified audio signals. In one embodiment the impedance is chosen to be substantially the same as the impedances of the sound transducers which are in use connected to the output connector. Advantageously, the impedance is a resistor, although e.g. an inductive coil can also be used.

Preferably, each amplification stage includes a variable gain control. In one embodiment, the variable gain controls of the amplification stages can be adjusted simultaneously and in a manner such that the variation is the same for each amplification stage. In another embodiment, the variable gain control of each amplification stage is independently adjustable.

Preferably, the accumulator chambers are located on a housing and separated by a distance wherein the diaphragms of the accumulators are facing outwardly from the housing.

In one embodiment the distance is a fixed distance whereas in another embodiment the distance can be variable.

Further, the amplification stages can be located within the housing and an the output connector can be located on the housing.

In one embodiment the device further includes two speakers which are each in use connected to one of the amplification stages via the connector, to transduce the amplified audio signal as a sound signal. Preferably, the two speakers are incorporated in headphones.

Preferably, the device is battery powered.

Advantageously, the device includes a power-on indicator which includes a high brightness blue light emitting diode (L.E.D.). This can provide a light source to e.g. elicit a pupillary response if required as part of accompanying neurological examination.

In accordance with a second aspect of the present invention there is provided a stethoscope, the stethoscope including two diaphragm type sound accumulator chambers, a microphone located in each accumulator chamber, an amplification stage connected to each microphone for electronically amplifying audio signals received by the microphone, and a transducer connected to each amplification stage for transducing the amplified audio signals as a sound signal, wherein the amplification stages are connected to one common earth potential and the negative inputs of the transducers are connected to the common earth potential via an impedance.

In one embodiment the impedance is chosen to be substantially the same as the impedances of the transducers. Advantageously the impedance is a resistor, although e.g. an inductive coil can also be used.

DETAILED DESCRIPTION OF PREFERRED EMBODIMENTS OF THE PRESENT INVENTION

Figure 1:
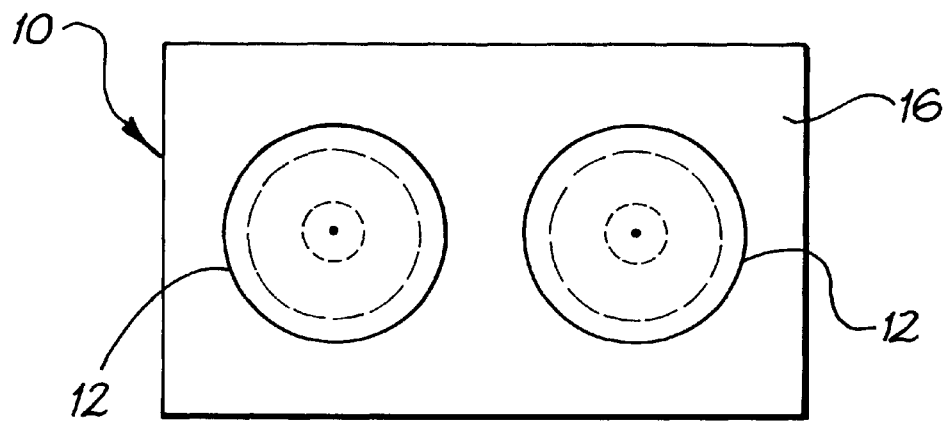
FIG. 1 is a bottom view of a stethoscope housing in accordance with one embodiment of the present invention.

As shown in FIG. 1, the device is incorporated into a housing 10 having two "Littman Cardiology II" TM type diaphragms 12 mounted on the base plate 16 of the housing 10. The diaphragms 12 are each centred over one of two microphones (not shown) for initial filtration of the sound signal received by the microphones (not shown). These selectively filter sound in the appropriate frequency range as in conventional stethoscopes utilising "Littman Cardiology II"TM type diaphragms, removing the need for more complex electronic bandpass filters. These also have the advantage that they can be made to alter their filtering characteristics toward that of a conventional stethoscope bell type pickup by simply increasing their application pressure.

Figure 2:
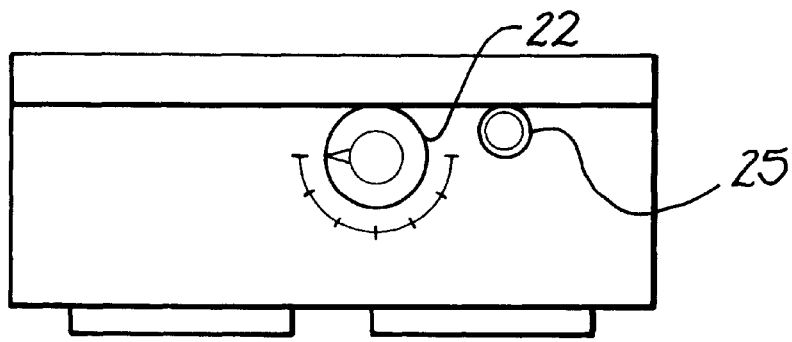
FIG. 2 is a front view of FIG. 1.
Figure 3:
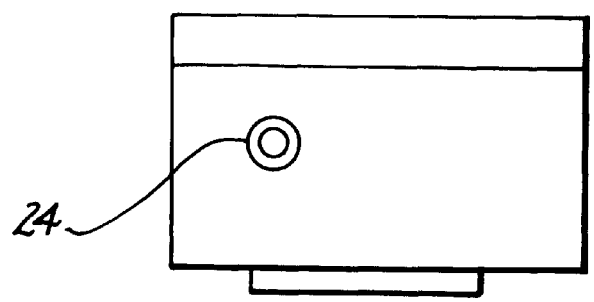
FIG. 3 is a side view of FIG. 1.

The sound thus filtered is transduced by the two electret type microphones 100 (FIG. 4) at a fixed separation of 50 mm, amplified by discrete preamplifier 102 and power amplifier 104 modules (FIG. 4) for each channel (incorporated within the housing 10 (with interposed volume control 22, FIG. 2). The output then terminates in a stereo 3.5 mm socket 24 (FIG. 3), allowing direct connection to headphones, signal processors or external speakers. Also, power-on indicator 25 (FIG. 2) is provided which includes a high brightness blue L.E.D., using only around 5 mA current, but powerful enough to e.g. elicit a pupillary response as part of accompanying neurological examination.

Figure 4:
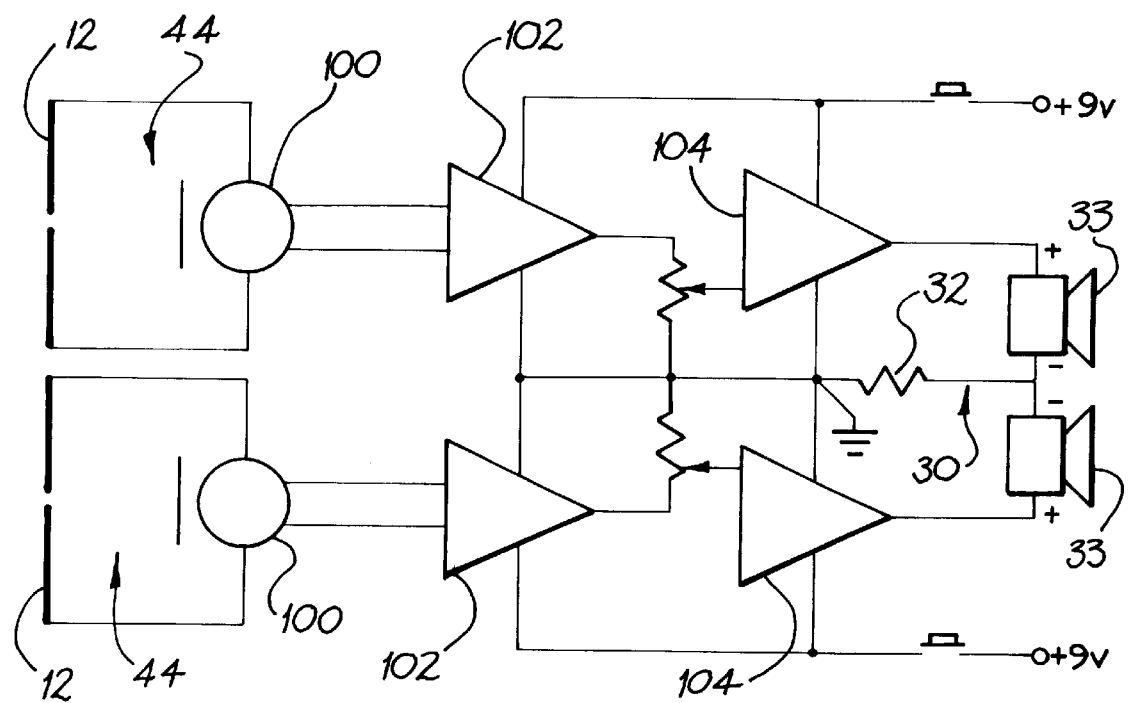
FIG. 4 is a circuit diagram of an electronic stereophonic stethoscope constructed in accordance with one embodiment of the present invention.

The electronic circuitry is outlined in FIG. 4. The common earth pathway 30 has been modified to enhance left and right channel separation.

A series resistor 32 in the common earth pathway 30 distal to the amplifier circuitry has been added. A resistance close to the impedances of the speakers 33 of e.g. a headphone (32 ohms in this case) gives rise to a useful effect which the applicant believes is due to a combination of the two following modes of operation for stereophonic amplification:

A) in conventional stereo amplification, both channels exist as discrete amplifier units without interaction, each unit amplifying whatever signal reaches it. In each channel, the amplifier circuitry and the speaker have a common earth connection (ie. resistor 32 in the common earth pathway 30 in FIG. 4 is omitted) and B) in amplifier circuits with passive earth/active output configuration, the negative input of the speaker of one channel is connected to the negative input of the speaker of the other channel but not to the common earth path, i.e. the common earth pathway 30 in FIG. 1 is open. In such an amplifier circuit, only difference signals (a signal greater in either left or right channels) produce an output at the speakers, with the sound in the opposite side speaker being 180 degrees out of phase. This gives rise to a peculiar "floating" effect, with no definite point source to the sound.

Combining the two effects by careful choice of earth pathway resistor 32 in the common earth pathway 30 in FIG. 4 may therefore give rise to a perceived broadening of sound separation due to a combination of:

boosted sound level (by 2.4 dB) on the side of a right or left only signal when compared to a signal reaching both channels, and some opposite phase current being transmitted to the opposing speaker in the event of difference signals, to help cancel out any softer signal occurring in this opposite side.

The applicant found that the effect is subtle but significant, further enhancing the stereo effect, and electronically placing the microphones further apart by emphasising the non-central sounds (with respect to the microphones).

Figure 5:
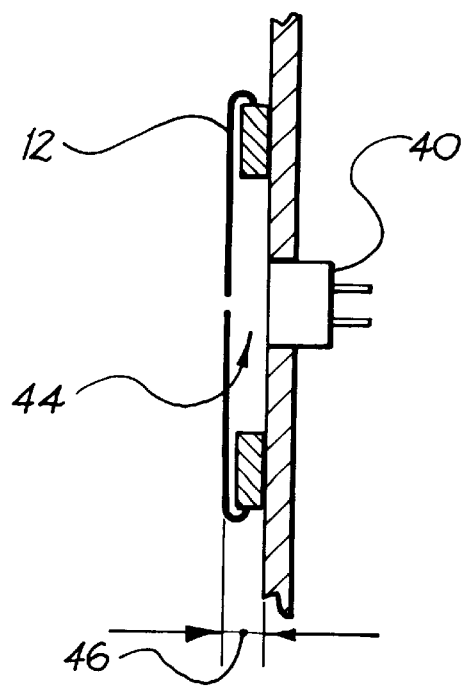
FIG. 5 is a detailed, cross-sectional view of one of the accumulator chambers depicted in FIG. 1.

In FIG. 5, the actual initial filtration has been achieved by placing the microphone 40 and diaphragm 12 in close proximity (e.g. distance 46=3 mm) within a accumulator chamber 44 formed between the diaphragm and the base plate 16. The diaphragms themselves come with a small hole at the front. Opening the chamber further greatly diminishes the bass response of the microphone.

The electret transducers used are not particularly sensitive at lower frequencies, but are amenable to mechanical amplification.

The dimensions of the housing 10 (see FIGS. 1, 2 and 3) of a prototype are 115 mm width by 60 mm hight by 45 mm depth. The circuit provides up to 500 milliwatts output per channel, however it will be appreciated by a person skilled in the art that miniaturisation of components can enable a decrease in size of the unit to dimensions and appearance approaching that of a conventional mechanical stethoscope.

Advantages over conventional stethoscopes are:

1) Single Application comparison of bilateral lung ventilation in a patient during application across the chest wall, provided that the distance between the diaphragms/microphones is adequately chosen.

2) Accurate localisation of demarcation between ventilated and unventilated segments of lung during collapse or obstruction in all age groups.

3) Spatial separation of cardiac sound:—the device makes it possible to identify transition of sounds from one cardiac area to another, potentially allowing very reliable diagnosis of flow murmurs, and also aiding localisation of cardiac valvular sounds:—by turning the device 90 degrees between applications this localising effect is further enhanced.

4) Ability to compensate for softened sounds (e.g. with obesity) by volume amplification.

5) Generalised subjective improvement in sound quality:—the two dimensional effect gives the impression of actually hearing from within the chest cavity rather than listening externally to it.

6) The most useful distance between the microphones appears to be 0.5 to 1 times the cardiac length.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The claims defining the invention are as follows:

1. A device for use in a stethoscope, the device including:

two diaphragm-type sound accumulator chambers;

one microphone located in each accumulator chamber;

one amplification stage connected to each microphone of electronically amplifying audio signals received by the microphones; and an output connector for outputting the amplified audio signals, wherein the amplification stages are connected to one common earth potential and the output connector is arranged in a manner such that negative inputs of sound transducers which are in use connected to the connector are connected to the common earth potential via an impedance.

2. A device in accordance with claim 1 wherein the impedance is chosen to be substantially the same as the impedances of the sound transducers which are in use connected to the output connector.

3. A device in accordance with claim 2 wherein the impedance is a resistor.

4. A device in accordance with claim 2 wherein each amplification stage includes a variable gain control.

5. A device in accordance with claim 4 wherein the variable gain controls of the amplification stages can be adjusted simultaneously and in a manner such that the variation is the same for each amplification stage.

6. A device in accordance with claim 4 wherein the variable gain control of each amplification stage is independently adjustable.

7. A device in accordance with claim 2, wherein the accumulator chambers are located on a housing and separated by a distance, and wherein diaphragms of the accumulators are facing outwardly from the housing.

8. A device in accordance with claim 7, wherein the distance is fixed.

9. A device in accordance with claim 7, wherein the distance is variable.

10. A device in accordance with claim 2, further including a power-on indicator which includes a high brightness blue light emitting diode (L.E.D.).

11. A stethoscope including:

two diaphragm-type sound accumulator chambers;

one microphone located in each accumulator chamber;

one amplification stage connected to each microphone for electronically amplifying audio signals received by the microphones;

and a transducer connected to each amplification stage for transducing the amplified audio signals as a sound signal, wherein the amplification stages are connected to one common earth potential and the negative inputs of the transducers are connected to the common earth potential via an impedance.

12. A stethoscope in accordance with claim 11, wherein the impedance is chosen to be substantially the same as the impedances of the transducers.

* * * * *